(12) United States Patent
Futatsugi et al.

(10) Patent No.: US 6,767,322 B1
(45) Date of Patent: Jul. 27, 2004

(54) ENDOSCOPE DEVICE (75) Inventors: Yasuyuki Futatsugi, Hachioji (JP);
Masakazu Higuma, Hachioji (JP);
Yosuke Yoshimoto, Hachioji (JP);
Ichiro Nakamura, Kokubunji (JP);
Takao Yamaguchi, Hachioji (JP);
Takeaki Nakamura, Hino (JP);
Takahiro Kishi, Yokohama (JP);
Yasuhito Kura, Hachioji (JP); Jun
Hiroya, Iruma (JP)

(73) Assignee: Olympus Corporation (JP)

( * ) Notice: Subject to any disclaimer, the term of this patent is extended or adjusted under 35 U.S.C. 154(b) by 27 days.

(21) Appl. No.: 09/588,704

(22) Filed: Jun. 6, 2000

(30) Foreign Application Priority Data

Jun. 8, 1999 (JP) ........................................ H11-161395

(51) Int. Cl.⁷ ................................................. A61F 1/05
(52) U.S. Cl. ...................................... 600/133; 600/129
(58) Field of Search ................. 600/109–110, 129–130, 600/133, 169

(56) References Cited

U.S. PATENT DOCUMENTS

| | | | | |
|---|---|---|---|---|
| 4,706,654 A | * | 11/1987 | Ogui | 600/130 |
| 4,799,613 A | * | 1/1989 | Adamson | 600/169 |
| 4,821,952 A | * | 4/1989 | Deciutiis | 600/129 |
| 4,838,246 A | * | 6/1989 | Hahn | 600/108 |
| 4,895,138 A | * | 1/1990 | Yabe | |
| 4,918,521 A | * | 4/1990 | Yabe | 600/109 X |
| 4,993,405 A | * | 2/1991 | Takamura | 600/110 |
| 5,212,595 A | * | 5/1993 | Dennison | 359/513 |
| 5,377,669 A | * | 1/1995 | Schulz | 600/121 |
| 5,599,278 A | * | 2/1997 | Hibbard | 600/133 |
| 6,080,101 A | * | 6/2000 | Tatsuro | 600/112 |
| 6,328,691 B1 | * | 12/2001 | Rudishhauser | 600/176 |
| 2002/0128539 A1 | * | 9/2002 | Higuma et al. | 600/133 |

FOREIGN PATENT DOCUMENTS

| | | |
|---|---|---|
| DE | 3740416 | 6/1989 |
| DE | 3740417 | 6/1989 |
| DE | 19713275 | 10/1998 |
| JP | 62-96616 | 6/1987 |
| JP | 62-212614 | 9/1987 |
| JP | 9-265046 | 10/1997 |

* cited by examiner

Primary Examiner—Nicholas D. Lucchesi
Assistant Examiner—Victor Hwang
(74) Attorney, Agent, or Firm—Ostrolenk, Faber, Gerb & Soffen, LLP

(57) ABSTRACT

A cover glass frame as a second frame body mounting thereto a cover glass is fitted onto an objective lens frame, which is a first frame body mounting thereto a tip end lens and an objective lens as optical members, in a manner to be movable in a direction of optical axis, and is fixed after having been adjusted in position in the direction of optical axis. The objective lens frame and the cover glass frame thus fitted and fixed are fitted into and joined to a cylindrical member to constitute an imaging unit, which is then arranged in a tip end portion of an insertion part of an endoscope. Thereby, focus adjustment can be performed on the optical members, which are assembled into the imaging unit, and a tip end side portion of the insertion part of the endoscope can be made small in outer diameter to prevent entry of vapor into the imaging unit even when autoclave sterilization is carried out.

39 Claims, 8 Drawing Sheets

ENDOSCOPE DEVICE

BACKGROUND OF THE INVENTION

1. Field of the Invention

The invention relates to an endoscope device affording the autoclave sterilization (high pressure and high temperature vapor sterilization).

2. Related Art Statement

These days, in the medical field, endoscopes inspecting a deep portion in a body are widely used for inspecting a deep portion in a body cavity by inserting an elongated insertion part into the body cavity or the like, and performing medical treatment by means of treatment tools as desired. It is essential to surely disinfect and sterilize these medical endoscopes to prevent the transmission of infectious disease or the like.

Conventionally, gases such as ethylene oxide gas and so on, and antiseptic solutions have been used for disinfecting and sterilizing. However, sterilizing gases or the like contain virulent poison as is well known, and so regulations have restricted their use to prevent environmental pollution. Also, another problem with sterilization is that endoscopes cannot be used immediately after sterilization because it takes time to perform aeration for removal of gases adhering to associated equipment after sterilization. Yet another problem is that these gases cause the running fee to become high.

On the other hand, the problem with antiseptic solutions is that managing antiseptic solutions is complex and troublesome and the disposal treatment of antiseptic solutions is expensive.

Hereupon, autoclave sterilization (high pressure and high temperature vapor sterilization) is recently prevailing as it can be used as sterilization of endoscope equipment immediately after sterilization without any troublesome operation and inexpensively.

A typical condition for autoclave sterilization includes American Standard Code ANSI/AAMI ST37-1992 approved by the Society of American Standard Code and published by the Society of Medical Equipment Research and Development, in which the pre-vacuum type prescribes a sterilization process at 132° C. for four minutes, and the gravity type prescribes a sterilization process at 132° C. for ten minutes.

However, a high pressure and high temperature vapor in such autoclave sterilization is transmitted through polymeric materials, such as rubber, plastics or the like—which constitute an endoscope—adhesives and so on. In particular, conventionally used adhesives such as epoxy resins are susceptible to deterioration by high temperature vapor, which results in peeling-off of an adhesive, such that it becomes possible for vapor to enter into the interior of a lens system.

Accordingly, where an endoscope of conventional watertight construction, made watertight, is loaded into an autoclave device for sterilization, vapor will enter the interior of the endoscope structure.

Also, to prevent an outer skin tube from bursting at a curved section during the vacuum process prior to the sterilization process, an endoscope may be charged into an autoclave sterilization apparatus with its outside and inside communication when autoclave sterilization is to be performed. However, by applying this method, vapor for autoclave sterilization will positively enter the endoscope.

In the case where autoclave sterilization is applied to an endoscope, in which an objective lens is fixed by means of an adhesive, disclosed in, for example, Japanese Utility Model Application No. 188081/1985, vapor will enter the objective optical system through the adhesive. Accordingly, when taking out such endoscope after the autoclave sterilization and inspecting the same under an eyepiece unit, the lens becomes frosted and appears white as fog. Such fog gradually clears, and so a normal image is observed.

However, while the lens remains foggy as described above, the endoscope cannot be used; therefor, there is a considerable inconvenience due to little progress in testing with the endoscope. Also, in the case where autoclave sterilization is repeatedly carried out or continuously carried out over a long time, such high pressure and high temperature vapor sterilization will cause the joined portions of the objective optical system to deteriorate thereby causing the joined portions of respective constituent parts, which are made of a stainless material to constitute the objective optical system, peel off from one another.

The phenomenon described above is the same with an electronic endoscope, in which CCDs are used as a solid-state image pickup element. Thus, when respective constituent parts of a stainless material on an imaging unit, which includes an objective optical system to be disposed at an end surface of an image incident end of the solid-state image pickup element such as CCDs, are joined together by a conventional adhesive, joined portions of the constituent parts deteriorate to allow entry, of vapor into an interior of the imaging unit, such that an image on a monitor will not appear normal due to fog or the like on the objective lens. Further, in the case where autoclave sterilization is repeatedly carried out or continuously carried out over a long time, joined portions of the respective constituent parts of the imaging unit peel off from one another.

To solve the above-mentioned problem, Japanese Patent Laid-Open No. 212614/1987 has proposed an endoscope of a gas-tight unit construction, in which a cover glass is gas-tightly mounted to an inner cylindrically-shaped armour member provided in an insertion part, and the optical members of an objective optical system or the like are mounted in the armour member to prevent fogging of the lens system of the optical members, deterioration of the lenses and the adhesive. In this prior art, the lens system is subjected to focus adjustment mounted to the armour member in a state.

Also, portions of an endoscope, which should prevent entry of vapor from autoclave sterilization, are gas-tightly joined by soldering, hard brazing, laser welding or the like. Also, in the case where optical members formed of, for example, optical glass are to be joined to a body tube, which is formed of a material such as ceramics to hold such optical members, metallic coating such as gold plating, nickel plating or the like is applied on joining surfaces, and then the joining surfaces are gas-tightly joined together by soldering, hard brazing, laser welding or the like. In addition, gas-tightness indicates one, which can withstand a high pressure and high temperature vapor for autoclave sterilization.

In the above-mentioned prior art, however, it is necessary to use a cover glass having a larger outer diameter than that of a lens in the objective optical system because the cover glass is installed on a tip end side of the objective optical system. Also, while the cover glass is made thin to enable reducing an outer diameter of a tip end of an insertion part of an endoscope to some degree, there are caused problems in the work of the cover glass, gas-tight joining, strength and so on when the cover glass is made thin. Therefore, the gas-tight unit construction is such that the cover glass is larger than the objective lens system. This leads to a great discomfort for a patient because the outer diameter of the tip of the endoscope which has a large angle of visibility and is also the insertion part of the endoscope becomes large.

Further, as described with respect to the prior art, because optical members and a body tube are generally different in coefficient of thermal expansion, the optical members are clamped by the body tube to sometimes break, crack and so on, due to a temperature difference at the time of heating for joining by hard brazing and soldering, and at the time of cooling after the joining when the optical members and the body tube are to be joined to each other by hard brazing, soldering or the like. Also, in some cases, heat produced at the time of the autoclave sterilization exerts forces tending to produce gaps in joined portions between the optical members and the body tube, which are different in coefficient of thermal expansion, such that the joined portions will peel off thereby undermining gas-tightness. Also, where a material such as cover or the like having a coefficient of thermal expansion near that of an optical glass, which is generally used to form optical members, is used to form a body tube, the range of selection for materials for the body tube is made narrow to cause an increase in cost.

The endoscope described in the above-mentioned Japanese Patent Laid-Open No. 212614/1987 needs to use a cover glass, having a larger diameter than that of an objective lens, on the tip end side of the objective lens system mounted to the optical frame provided on the insertion part. Therefore, a problem with such an endoscope is that an outer diameter on the tip of the insertion part becomes large to impose a great discomfort on a patient.

SUMMARY OF THE INVENTION

It is an object of the invention to provide an endoscope device capable of adjusting the focus of the optical members when assembled, making the outer diameter of a tip of the insertion part small, and preventing entry of vapor into the optical frame of the insertion part even when autoclave sterilization is performed.

Also, it is another object of the invention to provide an endoscope device capable of preventing optical members from being broken by a difference in coefficient of thermal expansion upon temperature change generated on the optical members and a body tube at the time of the optical members and the body tube are being joined together even when the optical members and the body tube have different in coefficients of thermal expansion, while and maintaining gas-tightness in the joined portions.

Further, it is another object of the invention to provide an endoscope device capable of preventing the joined portions from being broken due to a difference in their coefficients of thermal expansion by temperature changes generated on the optical members and the body tube at the time the autoclave sterilization is applied to the endoscope even when the optical members and the body tube have different coefficients of thermal expansion, while maintaining gas-tightness in the joined portions.

Also, it is another object of the invention to provide an endoscope device, which can perform focus adjustment on optical members as assembled, and make small a tip end portion of an insertion part in outer diameter to prevent entry of vapor into the tip end portion even when autoclave sterilization is carried out.

Also, it is another object of the invention to provide an endoscope device capable of preventing a cover glass and an objective lens frame (a first frame body) from being broken by temperature change generated on the cover glass and the objective lens frame when the cover glass and the objective lens frame are being joined together and when the autoclave sterilization is applied on an endoscope even when the cover glass and the objective lens frame have different coefficients of thermal expansion, while maintaining gas-tightness in the joined portions.

An endoscope device for autoclave sterilization, according to the instant invention, comprises a first unit composed of an optical member and having a first frame body for gas-tightly holding the optical member, the first unit being arranged at a tip end of the endoscope device; a second unit having a second frame body and a portion being adapted to fit on a fitting portion of the first unit and to be adhered and fixed thereto, the second unit arranged at a tip portion of the endoscope provided rearwardly of the first unit and cooperating with the first unit to constitute an optical unit; and a covering member having a first joined portion for gas-tight joining of the first frame body of the first unit, and a second joined portion for gas-tight joining of the second frame body of the second unit, the covering member covering the first frame body of the first unit and the second frame body of the second unit.

Also, an endoscope device for autoclave sterilization, according to the present invention, comprises a first frame body having gas-tightly mounted thereon an optical member, and arranged at a tip end of the endoscope device; a second frame body mounted to be movable in position relative to the first frame body in a direction of the optical axis, the second frame body being positionally adjustable in the direction of the optical axis to be made stationary; and a cylindrical member adapted, to cover the first frame body and the second frame body, and gas-tightly joined to the first frame body and the second frame body, respectively.

Further, an endoscope device for autoclave sterilization, according to the present invention, comprises a first metallic frame body having gas-tightly mounted thereon an optical member by brazing or soldering, and arranged at a tip end of the endoscope device; a second metallic frame body mounted to be movable relative to the first metallic frame body in a direction of the optical axis, the second metallic frame body being positionally adjustable in the direction of the optical axis to be made stationary; and a cylindrical member adapted to cover the first metallic frame body and the second metallic frame body, and gas-tightly joined to the first metallic frame body and the second metallic frame body, respectively.

Other features and advantages of the invention will be made adequately apparent from the following description.

DESCRIPTION OF THE DRAWINGS

FIGS. 1 to 10 are related to a first embodiment of the invention, FIG. 1 being a view showing an outward appearance of an electronic endoscope.

DETAILED DESCRIPTION OF THE PREFERRED EMBODIMENTS

Embodiments of the invention will now be described with reference to the drawings.

Figure 1:
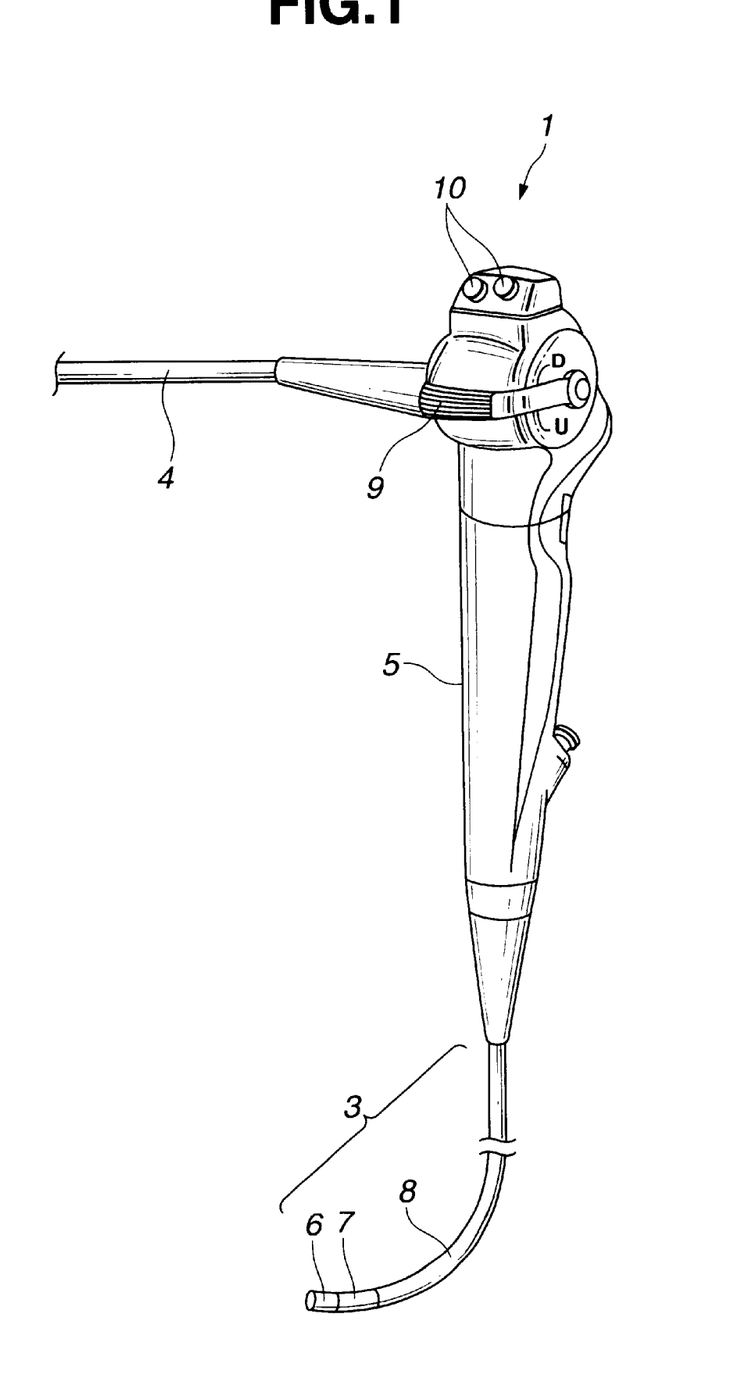
Figure 2:
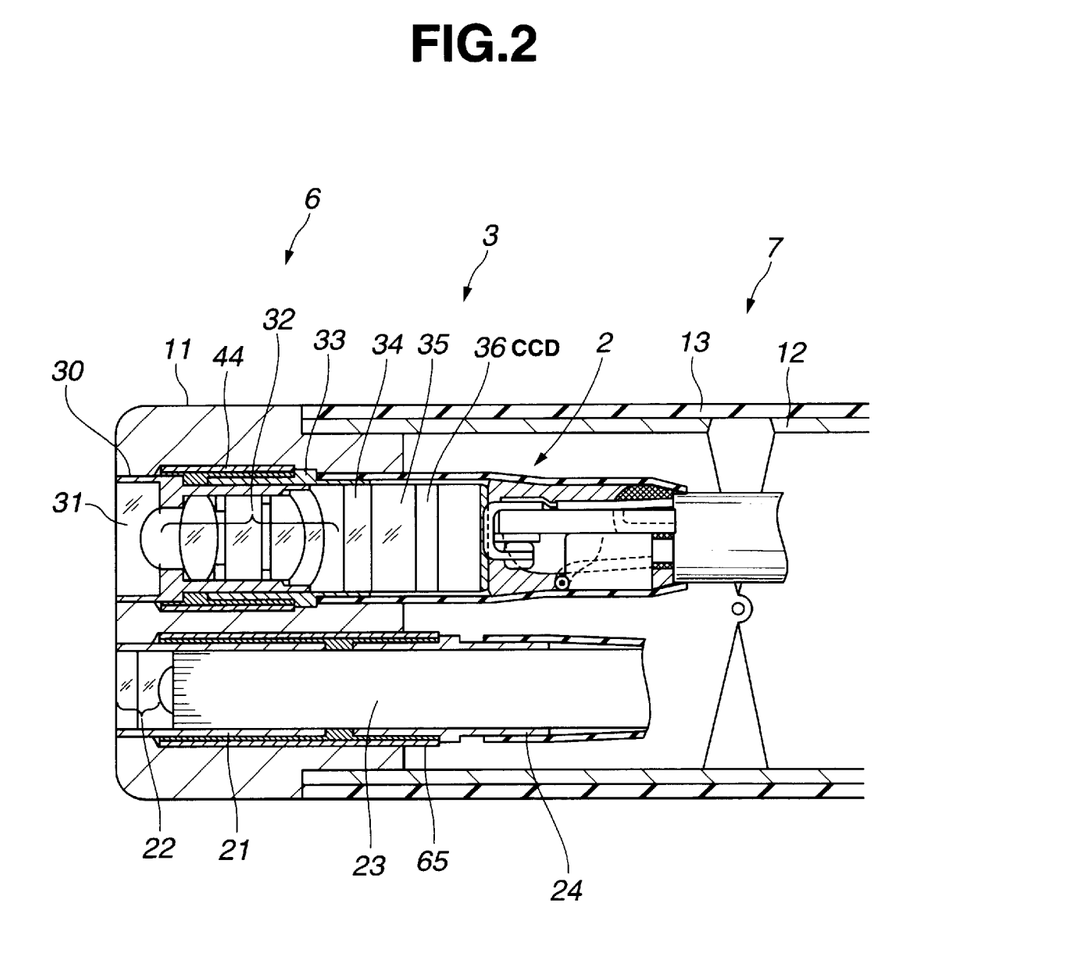
FIG. 2 is a cross sectional view illustrating a distal end portion of an inserting part of the endoscope.
Figure 3:
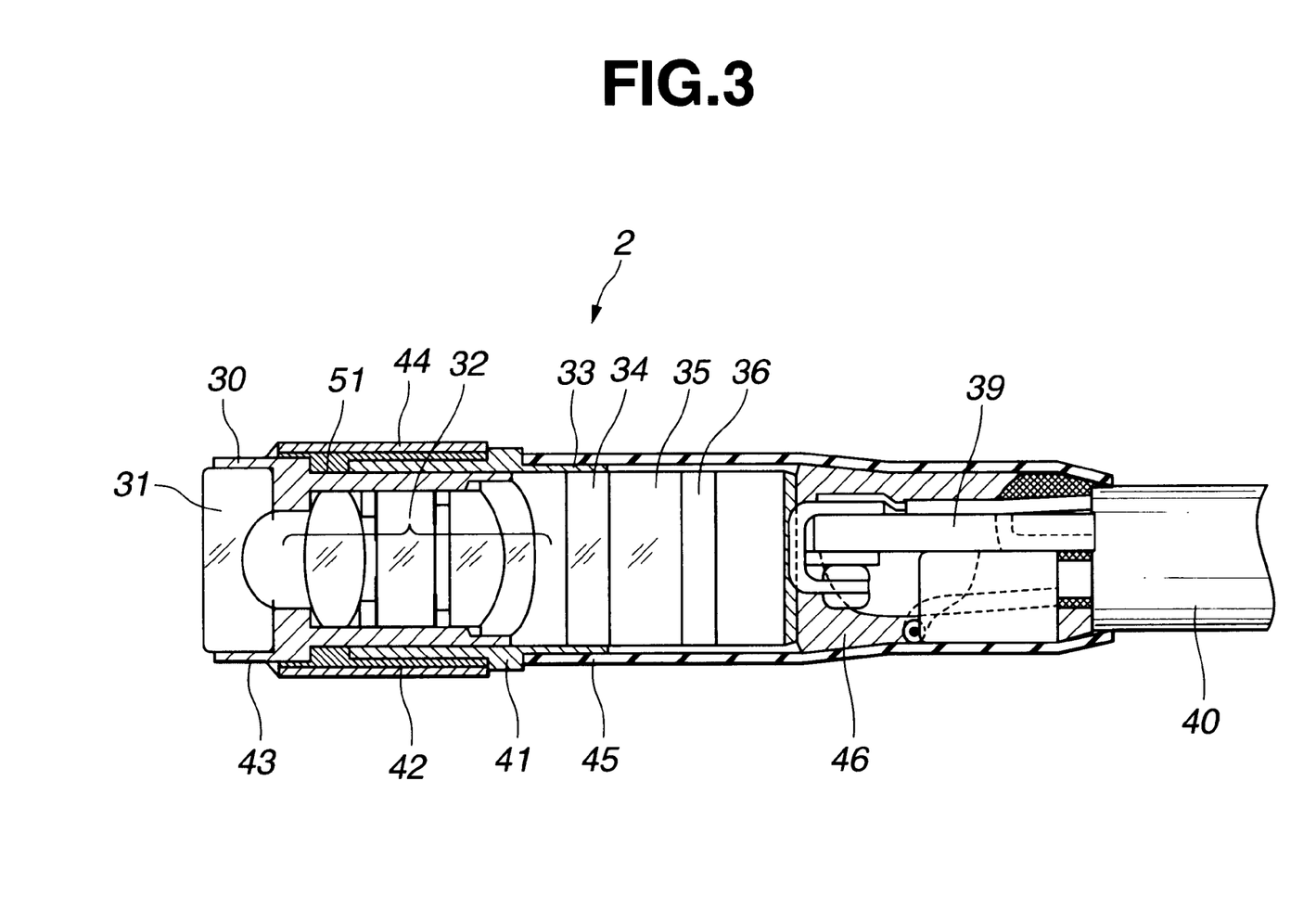
FIG. 3 is a cross sectional view illustrating an imaging unit in FIG. 2.
Figure 4:
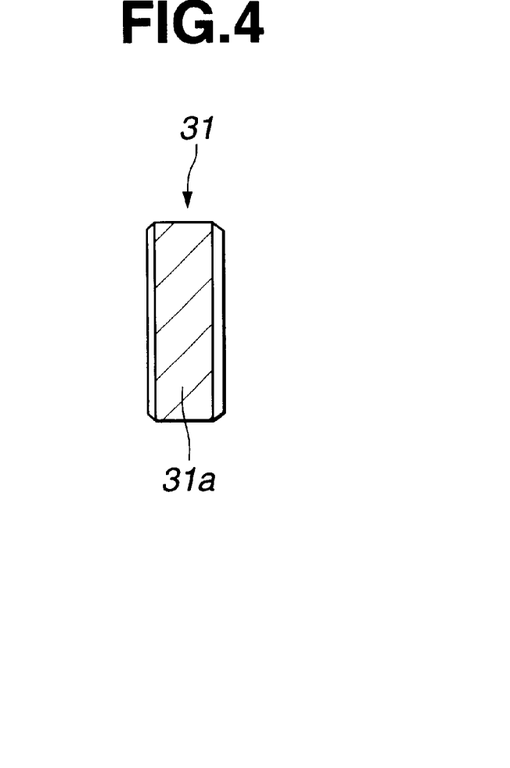
FIG. 4 is a view illustrating an outward appearance of a tip end lens of the imaging unit.
Figure 5:
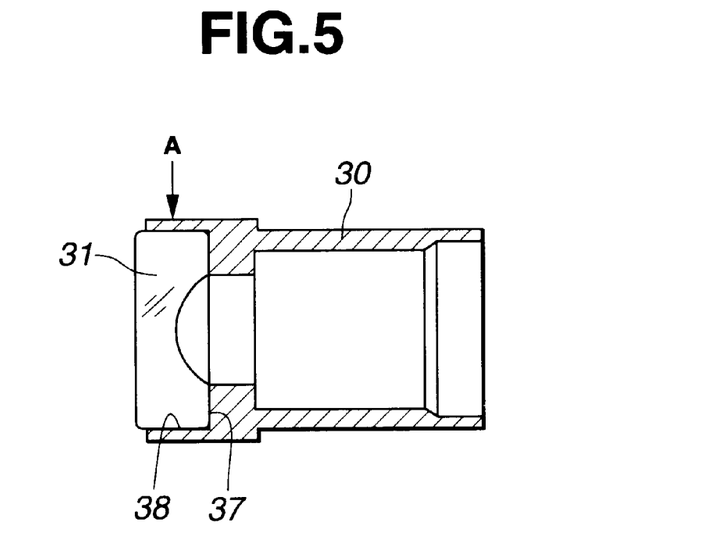
FIG. 5 is a cross sectional view illustrating a state, in which the tip end lens is assembled to a frame of an objective lens.
Figure 6A:
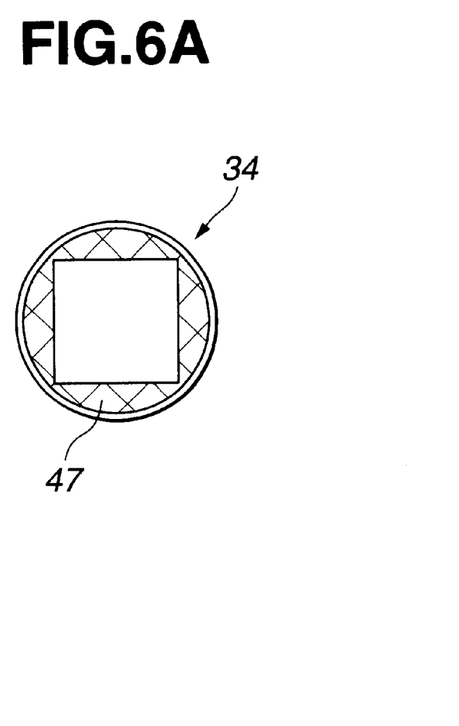
FIG. 6A is a front view illustrating a cover glass for the imaging unit.
Figure 6B:
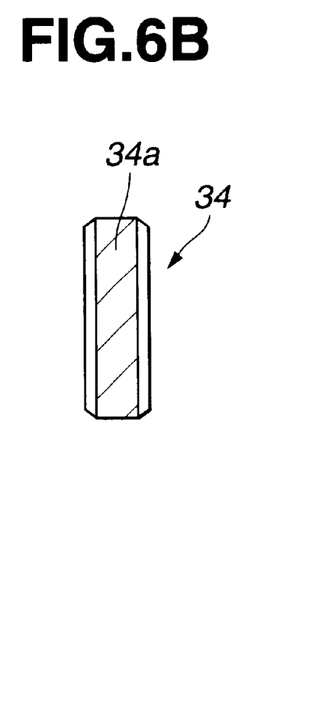
FIG. 6B is a side view illustrating the cover glass.
Figure 7:
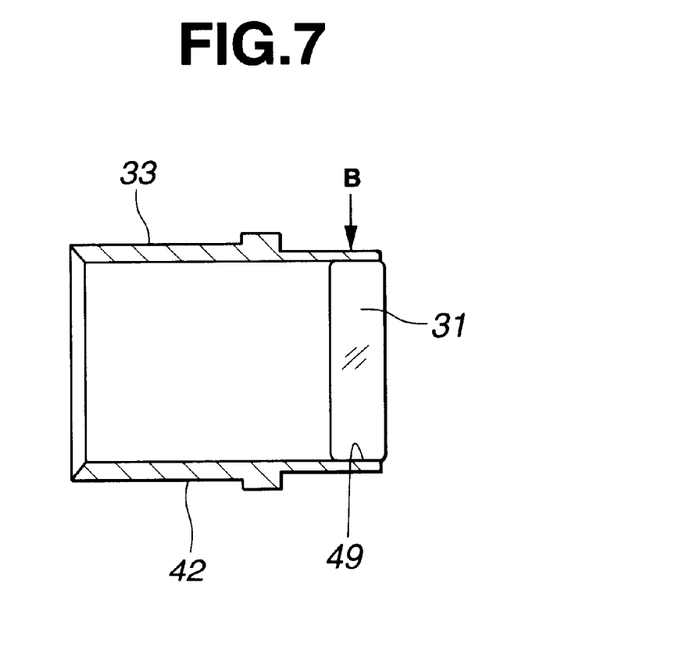
FIG. 7 is a cross sectional view illustrating the cover glass in FIG. 6 as assembled to a cover glass frame.
Figure 8:
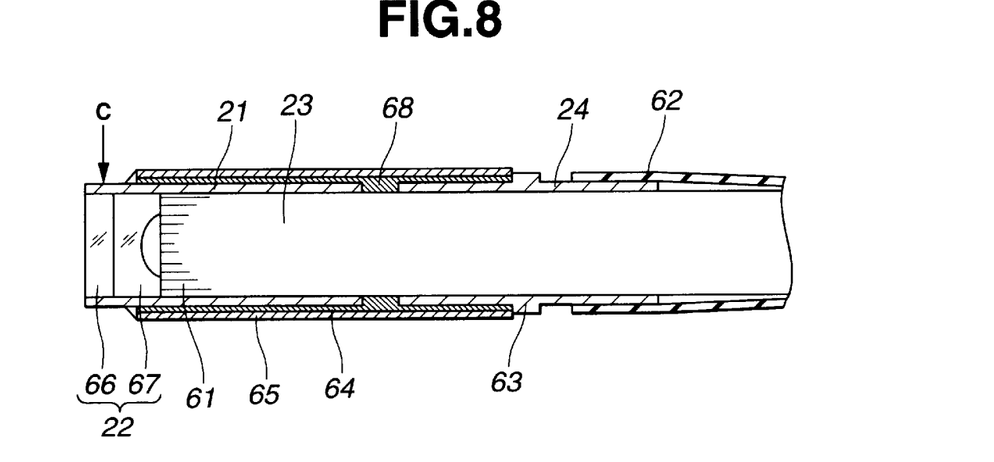
FIG. 8 is a cross sectional view illustrating a light guide in FIG. 3.
Figure 9:
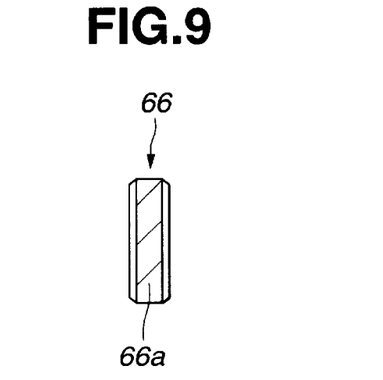
FIG. 9 is a view illustrating an outward appearance of the tip end lens of the light guide in FIG. 8.
Figure 10:
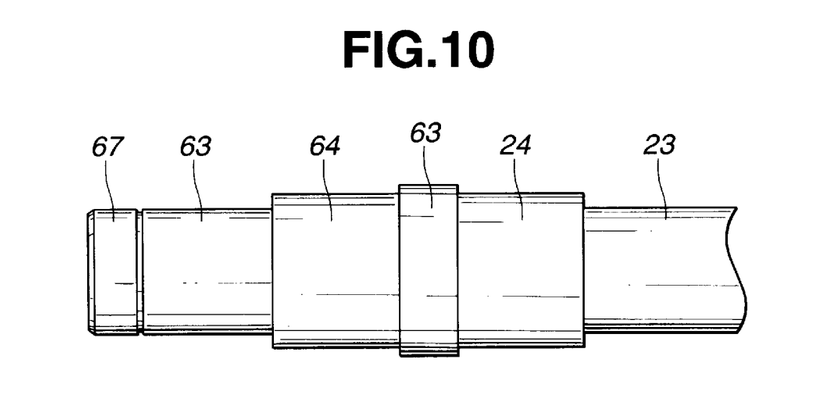
FIG. 10 is a view illustrating the outward appearance of the light guide of FIG. 8 and a rear end lens as assembled together.

FIGS. 1 to 10 inclusive are related to a first embodiment of the invention, FIG. 1 being a view illustrating an outward appearance of an electronic endoscope, FIG. 2 being a cross sectional view of a tip end portion of an inserting part of the endoscope, FIG. 3 being a cross sectional view of an imaging unit of FIG. 2, FIG. 4 being a view of an outward appearance of a tip end lens of the imaging unit, FIG. 5 being a cross sectional view of the tip end lens as assembled to a frame of an objective lens, FIGS. 6A and 6B each being a view of an outward appearance of a cover glass for the imaging unit, FIG. 6A being a front view of the cover glass, FIG. 6B being a side view of the cover glass, FIG. 7 being a cross sectional view of the cover glass of FIG. 6 as assembled to a cover glass frame, FIG. 8 being a cross sectional view of the light guide of FIG. 3, FIG. 9 being a view of an outward appearance of the tip end lens of the light guide of FIG. 8, and FIG. 10 being a view of the outward appearance of the light guide of FIG. 8 and a rear end lens as assembled together.

An electronic endoscope 1 (referred simply to as an endoscope) in the embodiment is water-tightly constructed to comprise an elongated insertion part 3 housing in a tip end thereof an imaging unit 2 described later, and an operating part 5, which is provided contiguous to a base end side of the insertion part 3 to serve as a handle part provided with a universal cord 4, which is provided to extend laterally and to which a light source device (not shown) and a video processor are mounted.

The insertion part 3 includes of a hard tip end portion 6 provided at its tip a freely bendable curved portion 7 provided on a base end side of the tip end hard portion 6, and a lengthy flexible tube portion 8 provided on a base end side of the curved portion 7. Provided rearwardly of the operating part 5 is a curved operating lever 9, which is turningly operated to enable bending the curved portion 7. Also, arranged on a rear end side of the operating part 5 are a suction button for operating a suction device (not shown) and switches 10, such as a release switch or the like, for making an image stationary.

The tip end side of the insertion part 3 of the endoscope will be described below with reference to FIG. 2.

The tip end hard portion 6 is made of a hard material, and formed from a substantially column-shaped tip end frame 11 formed with a through hole. Connected and fixed to a rear end of the tip end frame 11 as by soldering in a gas-tight manner is a curved tool 12, which is a main constituent member of the curved portion 7 and is made freely bendable by pivotally connecting a plurality of metallic cylindrical-shaped members together, and an outer periphery of which is covered by braid (not shown) of metallic mesh tube and a curved rubber tube 13. Both ends of the curved rubber tube 13 are gas-tightly fixed by wrap yarn and adhesive.

A light guide 23 for conducting light, which illuminates a subject through an illuminating lens system 22 mounted to an illuminating lens frame 21 on the tip end side, is fitted into a light guide mouth ring 24 to be arranged in the through hole of the tip end frame 11. Also, the through hole of the tip end frame 11 has the imaging unit 2 arranged therein. The imaging unit 2 takes in an optical image of the subject illuminated by the illuminating light through a tip end lens 31, which is mounted to an objective lens frame 30 to be exposed to an external face, and an objective lens system 32 mounted to a rear side of the tip end lens 31, and performs imaging through a cover glass 34 mounted to a cover glass frame 33 with the use of a solid-state image pickup element 36 (referred below to a CCD) that is adhered and fixed to a rear side of an infrared cut-off filter 35.

The illuminating light issued from the light source device (not shown) via the universal cord 4 to be conducted from the light guide 23 illuminates the subject of a portion being tested, from the illuminating lens system 22 on the hard tip end portion 6. An optical image of the subject as illuminated is taken in through the objective lens system 32 on the tip end hard portion 6, and is imaged by the CCD 36 through the cover glass 34 and the infrared cut-off filter 35 to be subjected to photoelectric conversion. A signal resulted from photoelectric conversion in the CCD 36 is transferred by a cable described later through the universal cord 4 to be subjected to signal processing by a video processor (not shown) to be displayed on a monitor.

In the embodiment, a cylindrically shaped member is fitted on the illuminating lens frame 21, which serves as a first frame body and has mounted thereto the illuminating lens system 22 as an optical member, and on the light guide mouth ring 24, which serves as a first frame body and fits therein the light guide 23. The illuminating lens frame 21 on the light guide 23 and the light guide mouth ring 24, respectively, are fitted into the cylindrically-shaped member. Alternatively, in the embodiment, the imaging unit 2 is constructed such that a cylindrically-shaped member is fitted onto the objective lens frame 30, which serves as a first frame body and has mounted thereto the tip end lens 31 and the objective lens system 32 as an optical member, and onto the cover glass frame 33, which serves as a second frame body and mounts thereto the cover glass 34. The objective lens frame 30 and the cover glass frame 33, respectively, are coupled to the cylindrically shaped member.

In addition, the imaging unit 2 comprises a frame body, in which the cover glass frame 33 as a second frame body can be fitted onto the objective lens frame 30 as a first frame body to be assembled thereto. Also, in the embodiment, the imaging unit 2 may be applied to arrange a second frame body, to which the CCD 36 is assembled and which can be adjusted in relative to a first frame body in a direction along the optical axis. Alternatively, the embodiment may be such that the imaging unit 2 arranges a second frame body, which can be fitted on and assembled to a first frame body and to which the CCD 36 is assembled.

First, the imaging unit 2 will be explained with reference to FIGS. 3 to 7.

As shown in FIG. 3, the tip end lens 31, which is mounted on the imaging unit 2 to be exposed to an external face, is formed by, for example, sapphire or glass having a high temperature vapor resistance, and is gas-tightly joined to the metallic objective lens frame 30. Surface treatment described later is applied to an outer peripheral surface (hatched portion in FIG. 4) of the tip end lens 31. Surfaces of the objective lens frame 30 are such that, for example, nickel is applied on a lower layer thereof, and a gold electroplating treatment is applied to an outermost layer thereof.

The objective lens system 32 is assembled and fixed to the objective lens frame 30 on the rear side of the tip end lens 31. The objective lens frame 30 fits thereinto the tip end lens 31 after an aperture opening 37 is placed therein.

The cover glass 34 comprising, for example, sapphire or glass having a high temperature vapor resistance, is provided on the rear end of the objective lens system 32, and gas-tightly joined to the metallic cover glass frame 33. The surface treatment described later in a similar manner to the tip end lens 31 is applied to the outer peripheral surface (hatched portion shown in FIG. 6B) of the cover glass 34.

Surfaces of the cover glass frame 33 are constructed like the objective lens frame 30 such that nickel is applied on a lower layer thereof, and a gold electroplating treatment is applied to an outermost layer thereof. In addition, in the embodiment, the objective lens frame 30 and the cover glass frame 33 are metallic, but may be made of a material, for example, ceramics, other than metal.

In this case, metallizing may be the same as that for the objective lens described later.

On the rear end side of the cover glass 34, the infrared cut-off filter 35 and the CCD 36 rearwardly of the infrared cut-off filter 35 are adjusted in the optical axis by reticle to be adhered and fixed in the manner described above. The CCD 36 mounts a substrate 39, on which electronic parts such as ICs and condensers are packaged, and is sealed by means of an adhesive having an insulating property. The CCD 36 and the substrate 39 assemble onto a length of cable 40. The length of cable 40 is connected to a terminal with a connector part (not shown) to be connected to a video processor (not shown).

The cover glass frame 33 is fitted onto the objective lens frame 30 and is moved along the optical axis to perform a focus adjustment for the objective lens system 32 and the CCD 36. After the focus adjustment, the objective lens frame 30 and the cover glass frame 33 are adhesively fixed to each other.

An abutting portion 41 is provided on an outer peripheral surface of the cover glass frame 33. The outer diameter of the outer peripheral surface 42 on the tip end side of the abutting portion 41 is substantially equal to a maximum outer diameter portion 43 of the objective lens frame 30. A tubular-shaped cylindrical member 44 having a cavity therein is fitted between the outer peripheral surface 42 on the tip end side of the abutting portion 41 and the maximum outer diameter portion 43 of the objective lens frame 30 in a manner to abut against the abutting portion 41. The tubular-shaped cylindrical member 44 is formed to have an inner diameter about 0.1 mm larger than the maximum outer diameter portion 43 of the objective lens frame 30 and an outer diameter of the outer peripheral surface 42 on the tip end side of the cover glass frame 33.

Solder is caused to flow into the gaps between the objective lens frame 30 and the tubular-shaped cylindrical member 44 and between the cover glass frame 33 and the tubular-shaped cylindrical member 44 to join them gastightly.

On the rear side of the cover glass frame 33, a heat shrinkable tube 45 covers an area extending from an outer peripheral portion of a rear side portion of the abutting portion 41 to a tip end side of the cable 40. The shinkable tube is filled with, for example, an epoxy-base adhesive 46.

Next, an explanation will be given to an assembling method, by which the tip end lens 31 is fitted into and gas-tightly joined to the objective lens frame 30. First, an explanation will be given regarding the surface treatment applied to an outer peripheral surface 31a of the tip end lens 31.

As shown in FIG. 4, the surface treatment applied to an outer peripheral surface 31a of the tip end lens 31 includes formation of a chromium film, which has a high adhesive property for sapphire or glass, on a lowermost layer (metallized layer) of the tip end lens 31. The chromium layer is formed by deposition or sputtering under vacuum. Also, a nickel layer is formed as an intermediate layer. An outermost layer is composed of a gold layer. While the gold layer may be formed by deposition or sputtering under vacuum, it can have a greater film thickness if formed by electroplating processing. The tip end lens 31 having subjected to the surface treatment in this manner is fitted into the objective lens frame 30 to be gas-tightly joined to the objective lens frame 30 as shown in FIG. 5.

The aperture opening 37 and the tip end lens 31 are placed in the objective lens frame 30, and laser beam from a laser device (not shown) is irradiated (from an arrow direction A in the drawing) on an outer peripheral surface of a fitting portion 38 of the objective lens frame 30, into which the tip end lens 31 is fitted.

The laser device utilizes, for example, a YAG laser susceptible of fine adjustment at a low output. The laser causes gold on the outer peripheral surface 31a of the tip end lens 31 and gold on the outermost layer of the objective lens frame 30, respectively, to melt to thereby be joined to each other when cooled. Such laser irradiation is effected over the entire periphery of the objective lens frame 30. Also, with irradiation by laser having a pulse wave, gas-tightness can be ensured by making overlapping of adjacent pulses 80% or more. Thereby, it is possible to join the tip end lens 31 and the objective lens frame 30 to each other while ensuring gas-tightness therebetween.

In addition, as a measure of joining the tip end lens 31 and the objective lens frame 30 to each other gas-tightly, joining can be effected by brazing and soldering without the use of a YAG laser. In this case, a slight gap in fitting portions between the tip end lens 31 and the objective lens frame 30 is provided, and solder or the like is made to flow into the gap.

Next, an explanation will be given to an assembling method for fitting the cover glass 34 into the cover glass frame 33 to join them together gas-tightly. First, an explanation will be given regarding the surface treatment applied to the cover glass 34.

As shown in FIG. 6A, the surface treatment applied to the cover glass 34 comprises formation of a mask 47, through which light does not transmit, by vacuum deposition or sputtering on a portion of a flat surface of the cover glass 34. For example, a three layer mask composed of chromium oxide/chromium/chromium oxide may be formed. An outer peripheral surface 34a of the cover glass 34 is subjected to a similar surface treatment to that of the tip end lens 31 as shown in FIG. 6B. A lowermost layer (metallized layer) has formed thereon a chromium film having a high adhesive property for sapphire or glass. The chromium film is formed by deposition or sputtering under vacuum. In addition, for example, a three layer mask composed of chromium oxide/chromium/chromium oxide may be formed like the same processing on the mask 47. Further, a nickel layer is formed as an intermediate layer, and a gold layer is formed as an outermost layer. While the gold layer may be formed by deposition or sputtering under vacuum, it can have a greater film thickness if formed by electroplating.

The cover glass 34 thus having been subjected to the surface treatment is fitted into and joined to the cover glass frame 33 in a gastight manner, as shown in FIG. 7.

The cover glass 34 is placed in the cover glass frame 33 to be positioned with a jig (not shown). A laser device (not shown) irradiates a laser beam (in a direction of an arrow B in the figure) on an outer peripheral surface of a fitting portion 49 of the cover glass frame 33, which fits the cover glass 34 thereinto. The laser causes gold on the outer peripheral surface of the cover glass 34 and gold on the outermost layer of the cover glass frame 33, respectively, to melt to thereby be joined to each other when cooled. Such laser irradiation is performed over the entire periphery of the cover glass frame 33.

Thereby, it is possible to ensure gas-tightness on the cover glass frame 33 and the cover glass 34 to join them together.

In addition, as way to gas-tightly join the cover glass frame 33 and the cover glass 34 together, brazing (brazing, soldering) can be used for joining both members without the use of laser. In this case, there is provided a slight gap in fitting portions between the cover glass frame 33 and the cover glass 34, and solder or the like is made to flow into the gap.

The objective lens frame 30, which joins the tip end lens 31, and the cover glass frame 33, which joins the cover glass 34 respectively, are gas-tightly fitted into the cylindrical member 44.

After the objective lens frame 30 and the cover glass frame 33 are fitted to each other to be subjected to focus adjustment, they are bonded to each other, flux is applied to necessary portions, and a ring-shaped solder is placed to reach the abutting portion 41. Thereafter the cylindrical member 44 is placed in position. Then, while load is applied on the cylindrical member 44 against the abutting portion 41, solder is melted by local heating with, for example, high frequency. Since the solder fills the gap due to surface tension, it fills between the objective lens frame 30 and the cylindrical member 44 and between the cover glass frame 33 and the cylindrical member 44 to form a solder layer 51. Thereby, joining can be achieved so as to maintain interiors of the respective parts gas-tight.

Also, the surface treatment, (formation of a nickel layer and a gold layer as an outermost layer to at least an inner peripheral surface of the cylindrical member 44 in the same manner as in the respective frames) improves the wettability of solder and makes is possible to omit flux depending upon a solder material and an atmosphere at the time of heating.

The above-mentioned assembly is preferably performed in an atmosphere of dry inert gas such as dry nitrogen gas, dry helium gas, dry argon gas or the like so as to prevent the atmosphere (in particular vapor) from mixing in an interior of the gas-tight structure. Such assembly may, however, be performed midway in the atmosphere depending upon setting of the assembling procedure, and a final assembly may be performed in the atmosphere of dry inert gap after replacement by the dry inert gas.

Next, the light guide 23 arranged in the insertion part 3 will be explained with reference to FIGS. 8 to 10.

As shown in FIG. 8, the light guide 23 has a formed, exposed portion 61 thereof assembled to the light guide mouth ring 24 of metal in a water-tight or gas-tight manner. The light guide 23 is covered over a substantially entire length thereof with a protective tube 62, a portion of a tip end of which covers the light guide mouth ring 24.

The light guide mouth ring 24 is provided on in outer peripheral surface thereof with an abutting portion 63 in the same manner as in the imaging unit 2. An outer diameter of an outer peripheral surface 64 on a tip end side of the abutting portion 63 of the light guide mouth ring 24 is substantially equal to an outer diameter of the illuminating lens frame 21. A tubular-shaped cylindrical member 65 having a cavity therein is fitted between the outer peripheral surface 64 on the tip end side of the abutting portion 63 and the illuminating lens frame 21 in a manner to abut against the abutting portion 63. The tubular-shaped cylindrical member 65 is formed to have an inner diameter larger, about 0.1mm for example, than the outer diameter of the illuminating lens frame 21 and an outer diameter of the outer peripheral surface 64 on the tip end side of the light guide mouth ring 24.

Solder is caused to flow into gaps between the illuminating lens frame 21 and the cylindrical member 65 and between the light guide mouth ring 24 and the cylindrical member 65 to join them gas-tightly.

The illuminating lens system 22 is composed of a tip end side illuminating lens 66 (see FIG. 9) and a rear end side illuminating lens 67, which are made of sapphire or glass having a high temperature vapor resistance (about 135 C). An outer peripheral surface 66a (hatched portion in FIG. 9) of the tip end side illuminating lens 66 is subjected to the same surface treatment as in the cover glass 34.

The light guide 23 and the rear end side illuminating lens 67 are made to be adhered to and fixed to each other with outer diameters thereof coinciding with each other as shown in FIG. 10.

A metallized layer is provided on the exposed portion 61 formed on the light guide 23, a nickel layer is formed as an intermediate layer, and a gold layer is formed as an outermost layer. An outermost layer is provided on at least an inner peripheral layer of the light guide mouth ring 24 to be composed of a gold layer. The light guide mouth ring 24 is fitted onto the surface treatment portion of the light guide 23, and a laser beam is irradiated on an outer peripheral surface of the light guide mouth ring 24 to melt and cool the gold on the light guide mouth ring 24 and the gold on the light guide 23. Thus, it is possible to gas-tightly join the light guide mouth ring 24 and the light guide 23.

Next, an explanation will be given regarding the procedure for assembling the light guide 23.

A jig (not shown) is used to position the tip end side illuminating lens 66 relative to the illuminating lens frame 21, and a laser device (not shown) irradiates a laser beam on an outer peripheral surface of the illuminating lens frame 21 (in a direction of an arrow C in the figure). The laser beam melts the gold of the surface treatment on the illuminating lens frame 21 and on the tip end side illuminating lens 66 and permits them to be cooled, thus joining both elements together gas-tightly. When the light guide 23 with the rear end side illuminating lens 67 mounted thereon is inserted into the illuminating lens frame 21 for adjustment of irradiation angle, the illuminating lens frame 21 and the light guide 23 are adhered and fixed to each other. Flux is applied to the outer peripheral surface of the illuminating lens frame 21, a tip end side outer peripheral surface 64 of the light guide mouth ring 24 and an inner peripheral surface of the cylindrical member 65, and a ring-shaped solder is made to fall down to an abutting portion 63 from the tip end side. Then, the cylindrical member 65 is fitted onto the tip end side outer peripheral surface 64 of the light guide mouth ring 24 and the illuminating lens frame 21 to reach the abutting portion 63. Subsequently, high frequency is used to melt the solder to permit the same to flow into gaps between the tip end side outer peripheral surface 64 of the light guide mouth ring 24 and the cylindrical member 65 and between the outer peripheral surface of the illuminating lens frame 21 and the cylindrical member 65, so that a solder layer 68 is formed in the respective gaps for joining the respective elements.

Thereby, gas-tight joining can be effected between the tip end side outer peripheral surface 64 of the light guide mouth ring 24 and the cylindrical member 65 and between the outer peripheral surface of the illuminating lens frame 21 and the cylindrical member 65.

Preferably, the above-mentioned assembly is performed in an atmosphere of dry inert gas such as dry nitrogen gas, dry helium gas, dry argon gas or the like as in the case of the imaging unit 2, and the atmosphere (in particular, vapor is prevented from mixing in the interior of the gas-tight structure. However, such assembly may be performed midway in the atmosphere depending upon setting of the assembling procedure, and a final assembly may be performed in the atmosphere of dry inert gas after replacement by the dry inert gas.

The endoscope 1 constructed in this manner is charged into a chamber (processing chamber) of an autoclave sterilization device (not shown). First, the interior of the chamber is placed under vacuum prior to sterilization. During the sterilization procedure, the chamber is filled with a high pressure and high temperature vapor, which then enters the interior of the endoscope 1 to make the same high in humidity. During the drying procedure, the chamber is vacuumized, and the interior of the endoscope 1 is made somewhat dry but not perfectly. No vapor enters the space, in which the objective lens system 32 of the imaging unit 2 and the illuminating lens system 22 of the light guide 23 are present, since the space is closely enclosed.

With the above-mentioned construction, the endoscope 1 in the embodiment presents the following effects.

(1) The optical members such as objective lenses, cover glass and so on are free from deterioration due to the autoclave sterilization (sterilization by high pressure and high temperature vapor), and are prevented from being frosted due to dew condensation caused by entry of vapor, so that the autoclave sterilization can be carried out repeatedly.

(2) Since the imaging unit 2, the light guide 23 and so on can be gas-tightly arranged on the tip end side of the endoscope insertion part 3 without the use of any cover glass, the outer diameter of the tip end of the insertion part 3 can be made small.

(3) Since no solder is used for gas-tight joining of the optical members, rust, frosting and deterioration of the optical members caused by entry of flux into the optical system are avoided.

(4) Since heating by laser and soldering with high frequency are local and instantaneous, the joining processing can be carried out even after parts (electronic parts, adhesives) without high temperature resistance are assembled in the vicinity of joining parts.

(5) Since the gas-tightly joined parts are hard (great bond strength of the surface treatment) to peel off due to thermal expansion during the autoclave sterilization and at the time of assembly, the autoclave sterilization can be carried out repeatedly.

(6) Since replacement with the dry inert gas is effected at the time of assembly, no vapor is existent in the interior of the lens units, so that frosting will not be caused even when the endoscope is rapidly cooled.

In addition, the invention is applied to the imaging unit 2 and the light guide 23, which are arranged in an elastic endoscope with the bendable curved portion 7 in the insertion part 3, such that, for example, in the imaging unit 2, the cylindrical member 44 is fitted onto the objective lens frame 30 as a first frame body and the cover glass frame 33 as a second frame body to be gas-tightly joined to the same. However, the invention is not limited to such arrangement. For example, the invention can be applied to various optical systems, such as a hard endoscope with a hard insertion part, a fiber scope, which transfers an image by way of a bundle of optical fibers, an exterior type camera and so on, such that a cylindrical member is fitted onto a first frame body with optical members mounted thereon and a second frame body, which is adjustable in position relative to the first frame body in a direction of optical axis, and the first frame body and the second frame body, respectively, are joined to the cylindrical member. Also, the cylindrical member may be fitted onto the first frame body with optical members mounted thereon and the second frame body, which can be fitted on and mounted to the first frame body, and the first frame body and the second frame body, respectively, may be joined to the cylindrical member.

Also, the endoscope 1 according to the invention is not limited to the above-mentioned embodiment, but is susceptible of various modifications within the scope of the invention.

Figure 11:
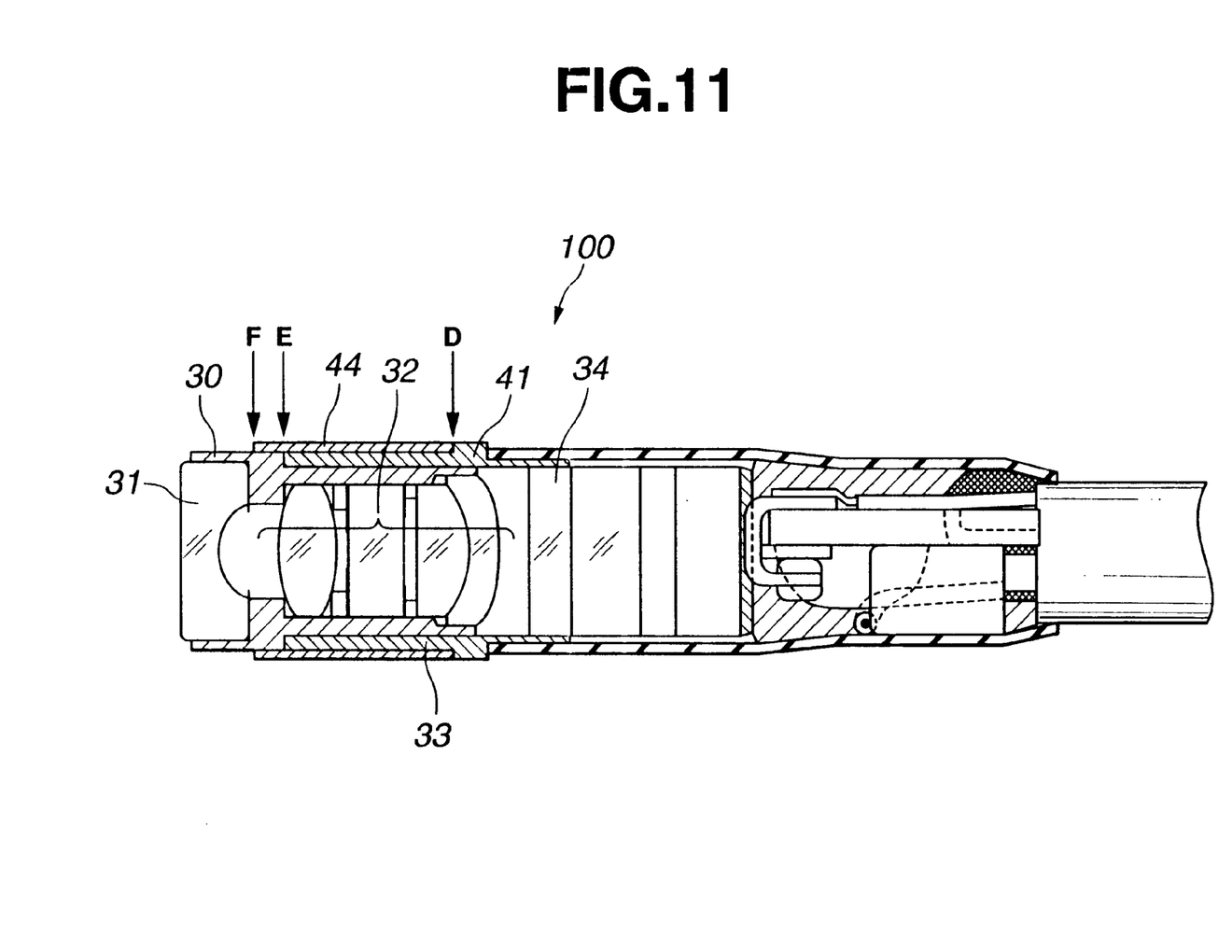
FIG. 11 is a cross sectional view illustrating an imaging unit according to a second embodiment of the invention.

FIG. 11 is a cross sectional view illustrating an imaging unit according to a second embodiment of the invention.

With the imaging unit 2 according to the first embodiment, the cylindrical member 44 is fitted onto the objective lens frame 30 as a first frame body with the tip end lens 31 and the objective lens system 32 mounted thereon, and onto the cover glass frame 33 as a second frame body with the objective lens frame 30 and the cover glass 34 mounted thereon, and solder is made to flow between the objective lens frame 30 and the cylindrical member 44, and between the cover glass frame 33 and the cylindrical member 44 to form the solder layer 51 for gas-tight joining. In the second embodiment, laser is irradiated on joined portions between the objective lens frame 30 and the cylindrical member 44, and between the cover glass frame 33 and the cylindrical member 44 to effect butt welding for the joining. Other constitution than that described above is substantially the same as that shown in FIG. 3, and so an explanation is omitted. The same reference numerals designate the same constituents.

An imaging unit 100 in the second embodiment is similar to the imaging unit 2 of the FIG. 3 in that the cylindrical member 44 is fitted between the outer peripheral surface 42 on the tip end side of the abutting portion 41 of the cover glass frame 33 and the maximum outer diameter portion 43 of the objective lens frame 30 in a manner to abut against the abutting portion 41. In addition, the cylindrical member 44 has an inner diameter, which eliminates a difference between it and an outer diameter of the maximum outer diameter portion 43 of the objective lens frame 30 as much as possible, and is set in accordance with the assembling property and limits on work allowances. Other constitution than that is substantially the same as that shown in FIG. 3 and so is omitted. Now an explanation will be given to an assembling method.

Butt welding is performed by irradiating laser beam (in the direction of the arrow D in the figure) from a laser device (not shown) on an area where the abutting portion 41 and the cylindrical member 44 abut against each other. In addition, when performing butt welding on the abutting portion 41 and the cylindrical member 44, some clearance may be provided between an outer diameter of the outer peripheral surface 42 on the tip end side of the abutting portion 41 and an inner diameter of the cylindrical member 44. In this case, assembling of the cylindrical member 44 is made easy.

Then, piercing welding is carried out by irradiating laser beam (in the direction of the arrow E in the figure) on an area where the cylindrical member 44 is fitted onto the maximum outer diameter portion 43 of the objective lens frame 30. At this time, if welding is visually confirmed, it is possible to perform fillet welding by irradiating laser beam on an end of the cylindrical member 44 (in the direction of the arrow F in the figure). Also, piercing welding may be performed on the objective lens frame 30 and the cylindrical member 44, and on the cover glass frame 33 and the cylindrical member 44 under the same condition. In this case, work ability is improved in laser welding.

As a result, more gas-tight joining can be applied on the objective lens frame 30 and the cylindrical member 44, and on the cover glass frame 33 and the cylindrical member 44 as compared with the imaging unit 2 in the first embodiment. Thus, entry of vapor can be prevented even when autoclave sterilization is effected.

Figure 12:
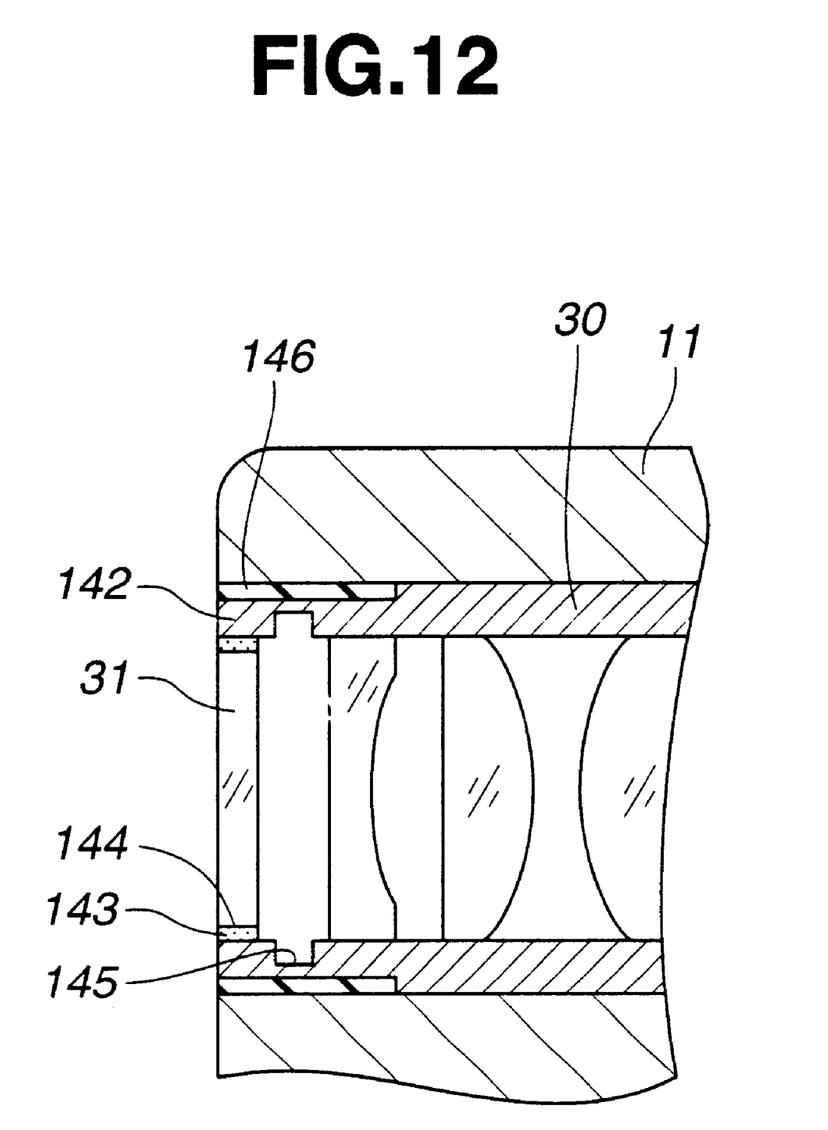
FIG. 12 is a cross sectional view illustrating a tip end of an electronic endoscope according to a third embodiment of the invention.

FIG. 12 is a cross sectional view illustrating a portion of a tip end of an endoscope according to a third embodiment of the invention.

Here, while a cover glass frame (second frame body) fitted rearwardly of the objective lens frame 30 (first frame body) and a cylindrical member, which covers the objective lens frame 30 and the cover glass frame, are omitted in FIG. 12, they are fundamentally the same as those shown in FIG. 2.

Metallizing processing such as gold plating, or nickel plating is applied on an outer peripheral surface of a cover glass 31, and a joined portion 144 for joining the cover glass 31 and a tip end portion 142 of a body tube together as by hard brazing is provided in a gap 143 between that surface of the cover glass 31, which is applied by the metallizing processing, and an inner periphery of the tip end portion 142 of the objective lens frame 30. In addition, the joined portion 144 may be formed by soft brazing such as soldering than the hard brazing. The joined portion 144 serves to provide gas-tight joining between the cover glass 31 and the tip end portion 142 of the objective lens frame 30 to prevent entry of a gas such as a high pressure and high temperature vapor during the autoclave sterilization.

A groove is formed on an inner periphery of the objective lens frame 30 rearwardly of the joined portion 144, that is, an inner periphery of the objective lens frame 30 rearwardly of the tip end portion 142, whereby a thin walled portion 145 is formed to have a smaller wall thickness than other portions of the objective lens frame 30. Since the thin walled portion 145 is formed on the objective lens frame 30, forces caused by a portion of the objective lens frame 30 rearwardly of the thin walled portion 145 expanding and contracting due to heat are buffered by the thin walled portion 145, so that forces transmitted to the tip end portion 142 of the lens frame will be reduced. That is, forces caused by the objective lens frame 30 expanding and contracting due to heat of high pressure and high temperature vapor for the autoclave sterilization are weakened toward the joined portion 144. And an elastic adhesive layer 146 of, for example, silicone base is provided in a gap between a portion near the tip end of the objective lens frame 30 and the tip end frame 11 to absorb forces caused by deformation of the thin walled portion 145 and the tip end portion 142 of the lens frame.

Next, the joining of a cover glass 31 to the objective lens frame 30 will be explained.

The cover glass 31, an outer peripheral surface of which is subjected to the metallizing processing, is fitted into an inner periphery of the tip end 142 of the objective lens frame 30, and a melted brazing metal is made to flow into a gap 143 therebetween. Then the cover glass 31 and the objective lens frame 30, respectively, are heated to expand. At this time, the objective lens frame 30 expands more than the cover glass 31 due to a difference between the coefficient of thermal expansion of the cover glass 31 and that of the objective lens frame 30, and the gap 143 between the cover glass 31 and the objective lens frame 30 spreads to permit the brazing metal to fill therein. Then, when heating of the brazing metal is stopped, the metal solidifies, and the cover glass 31 and the objective lens frame 30 are made to be cooled and to contract. Then, since the objective lens frame 30 generally contracts more rapidly than the cover glass 31, the latter is clamped by the former. However, the objective lens frame 30 in the embodiment is formed with the thin walled portion 145 near and rearwardly of the tip end 142 thereof, and forces caused by the contraction of the portion of the objective lens frame 30 rearwardly of the thin walled portion 145 are buffered by the thin walled portion 145, so that forces, with which the objective lens frame 30 clamps the cover glass 31 at the tip end portion 142 of the lens frame will be reduced. With the above arrangement, the joined portion 144 is formed while breakage of the cover glass 31 such as cracking or the like is prevented.

Next, the condition around the joined portion 144 between the cover glass 31 and the objective lens frame 30 when the autoclave sterilization is applied on the endoscope 1 will be given.

When the autoclave sterilization is applied on the endoscope 1, high pressure and high temperature vapor filled around the endoscope 1 heats the cover glass 31 and the objective lens frame 30 to expand the same. At this time, the objective lens frame 30 generally expands more than the cover glass 31, and forces caused by the expansion of the portion of the objective lens frame 30 rearwardly of the thin walled portion 145 are buffered by the thin walled portion 145, thereby forces caused by the objective lens frame 30 expanding at the tip end portion 142 of the lens frame are reduced. Accordingly, expanding of the gap 143 is suppressed, and so breakage due to peeling-off of the joined portion 144 or the like is prevented.

Also, a front end of the objective lens frame 30 is gas-tightly sealed by the cover glass 31 joined to the objective lens frame 30 at the joined portion 144, so that the high pressure and high temperature vapor for the autoclave sterilization is prevented from entering the objective lens frame 30.

As described above, according to the embodiment, even if the cover glass 31 and the objective lens frame 30 have different coefficients of thermal expansion from each other, breakage of the cover glass 31 such as cracking or the like is prevented when the cover glass 31 and the objective lens frame 30 are joined to each other.

Also, even if the cover glass 31 and the objective lens frame 30 have different coefficients of thermal expansion from each other, the joined portion 144 can be prevented from breakage by the autoclave sterilization applied to the endoscope 1.

Therefore, according to the embodiment, even if the coefficients of thermal expansion of the cover glass 31 and the objective lens frame 30 are different from each other, the cover glass 31 and the joined portion 144 can be prevented from being broken by temperature change generated on the cover glass 31 and the objective lens frame 30 when the cover glass 31 and 37 the objective lens' frame 30 are joined together, and when the autoclave sterilization is applied to the endoscope 1, and gas-tightness on the joined portion 144 can be maintained.

Also, when the autoclave sterilization is applied on the endoscope 1, forces exerted on the joined portion 144 are reduced, so that metal fatigue or the like, of the joined portion 144 caused by the repeated application of autoclave sterilization on.the endoscope 1, is decreased, and hence the durability joined portion 144 is improved.

Also, since breakage of the joined portion 144 and the cover glass 31 is prevented in the above manner, entry of vapor into the objective lens frame 30 is prevented when the autoclave sterilization is applied to the endoscope 1, thereby preventing deterioration, due to vapor, of the optical members such as the objective lens frame 30, the objective lens system 32 received in the cover glass frame 33, and so on, CCDs, a circuit substrate, and wiring.

Also, since breakage of the cover glass 31 can be prevented when the cover glass 31 and the objective lens frame 30 are joined together, yield at the time of joining them is enhanced to enable reduction in cost.

Further, since the objective lens frame 30 may be different in coefficient of thermal expansion from the cover glass 31, selection of a material for the objective lens frame 30 is enlarged, so that cost reduction can be achieved.

In addition, the endoscope 1 is not limited to a soft endoscope having a soft insertion part but may be a hard endoscope having a hard insertion part.

Also, the objective lens frame 30 may be made of covar, ceramics or the like.

In addition, while not shown, the above-mentioned arrangement may be applied to the light guide 23 described in the first embodiment such that butt welding is performed by causing a laser device (not shown) to irradiate laser beam on an area where the abutting portion 63 on the light guide mouth ring 24 abuts against the cylindrical member 65, and piercing welding is performed by irradiating laser beam on an area where the cylindrical member 65 is fitted onto the outer peripheral surface of the illuminating lens frame 21, whereby more gas-tight joining is provided between the illuminating lens frame 21 and the cylindrical member 65 and between the light guide mouth ring 24 and the cylindrical member 65. Also, the endoscope 1 according to the invention is not limited to the above-mentioned embodiments, but is susceptible of various modifications, such as an objective lens, an eyepiece part and a camera adapter, detachably mounted to the eyepiece part, of a fiber scope, which transfers an image by way of a bundle of optical fibers, within the scope of the invention.

It is apparent that different embodiments in a wide range can be practiced in the invention within the spirit and scope of the invention. The invention is not limited to particular embodiments but to the appended claims.

What is claimed is:

1. An endoscope for autoclave sterilization, comprising:
    a first unit comprised of an optical member and a first frame body, the first frame body including an extension portion, a joining portion, and an optical receiving portion for gas-tightly receiving the optical member, the optical receiving portion having an outer diameter;
    a second unit having a second frame body, the second frame body including a joining portion and an abutting portion positioned rearwardly of the joining portion, an outer diameter of the abutting portion being larger than an outer diameter of the joining portion of the second frame body, the outer diameter of the joining portion of the second frame body being substantially the same as the outer diameter of the optical receiving portion of the first frame body, the joining portion of the first frame body being fitted in an interior of the joining portion of the second frame body; and
    a covering member disposed over and gas-tightly joined with the extension portion of the first frame body and the abutting portion of the second frame body, an inner diameter of the covering member being substantially the same as the outer diameters of the optical receiving portion of the first frame body and the joining portion of the second frame body;
    wherein the first frame body, the second frame body and the covering member are joined integrally and gas-tightly by one of soldering, brazing and welding between the first frame body and the covering member and between the second frame body and the covering member.

2. The endoscope according to claim 1, wherein the first unit includes an objective lens system, the first unit and the second unit being joined at a position that focuses the objective lens system and a solid state image pickup device.

3. The endoscope according to claim 2, wherein the second frame body encloses the first frame body.

4. The endoscope according to claim 2, wherein the second frame body of the second unit gas-tightly holds the solid-state image pickup device.

5. The endoscope according to claim 4, wherein the solid-state image pickup device comprises a solid-state image pickup element and a glass body arranged forwardly of the solid-state image pickup element, and the glass body and the second frame body of the second unit are gas-tightly held.

6. The endoscope according to claim 1, wherein the second frame body encloses the first frame body.

7. The endoscope according to claim 1, wherein the second frame body of the second unit gas-tightly holds a solid-state image pickup device.

8. The endoscope according to claim 7, wherein the solid-state image pickup device comprises a solid-state image pickup element and a glass body arranged forwardly of the solid-state image pickup element, and the glass body and the second frame body of the second unit are gas-tightly held.

9. The endoscope according to claim 1, wherein the first frame body has a portion that is joined with the optical member and the first frame body has a thin wall portion disposed rearwardly of the portion that is joined to the optical member, the thin wall portion buffering stress transmitted to the joined portion due to a change in temperature.

10. The endoscope according to claim 9, wherein the thin wall portion is capable of buffering stress during a change in temperature when the first frame body is joined to the optical member.

11. The endoscope according to claim 9, wherein the thin wall portion is capable of buffering stress during a change in temperature when the endoscope is subjected to autoclave sterilization.

12. The endoscope according to claim 1, wherein the second unit further comprises an imaging unit.

13. The endoscope according to claim 1, wherein the covering member comprises a cylindrical member.

14. The endoscope according to claim 1, wherein the covering member, the first frame body and the second frame body are joined gas-tightly by welding.

15. The endoscope according to claim 1, wherein the covering member is gas-tightly joined with the first frame body and the second frame body by butt welding.

16. The endoscope according to claim 1, wherein a solder layer is formed between the covering member and the first frame body and the second frame body to join them gas-tightly.

17. An endoscope device for autoclave sterilization, comprising:

an insertion part, the insertion part having a distal free end; and an optical unit on the insertion part, the optical unit including:

a first frame body disposed at the distal free end of the insertion part and including an extension portion, a joining portion, and an optical receiving portion for gas-tightly receiving an optical member, the optical receiving portion having an outer diameter;

a second frame body including a joining portion and an abutting portion positioned rearwardly of the joining portion, an outer diameter of the abutting portion being larger than an outer diameter of the joining portion of the second frame body, the outer diameter of the joining portion of the second frame body being substantially the same as the outer diameter of the optical receiving portion of the first frame body, the joining portion of the first frame body being fitted in an interior of the joining portion of the second frame body; and a cylindrical member disposed over and gas-tightly joined with the extension portion of the first frame body and the abutting portion of the second frame body, an inner diameter of the cylindrical member being substantially the same as the outer diameters of the optical receiving portion of the first frame body and the joining portion of the second frame body wherein the first frame body, the second frame body and the cylindrical member are joined integrally and gas-tightly by one of soldering, brazing, and welding between the first frame body and the cylindrical member and between the second frame body and the cylindrical member.

18. The endoscope according to claim 17, wherein plating processing is applied on surfaces of at least one of the first frame body, the second frame body, and the cylindrical member.

19. The endoscope according to claim 18, wherein the plating processing comprises nickel plating on a lower layer, and gold electroplating on an outermost layer.

20. An endoscope for autoclave sterilization, comprising:

an insertion part, the insertion part having a distal free end; and an optical unit on the insertion part, the optical unit including:

a first metallic frame body disposed at the distal free end of the insertion part and including a joining portion and an optical receiving portion for gas-tightly receiving an optical member by one of brazing and soldering, the optical receiving portion having an outer diameter;

a second metallic frame body including a joining portion and an abutting portion positioned rearwardly of the joining portion, an outer diameter of the abutting portion being larger than an outer diameter of the joining portion of the second frame body, the outer diameter of the joining portion of the second frame body being substantially the same as the outer diameter of the optical receiving portion of the first frame body, the joining portion of the first frame body being fitted in an interior of the joining portion of the second frame body;

a cylindrical member disposed over and gas-tightly joined with the first metallic frame body and the second metallic frame body, the cylindrical member being fitted to abut against the abutting portion of the second metallic frame body, an inner diameter of the cylindrical member being substantially the same as the outer diameters of the optical receiving portion of the first frame body and the joining portion of the second frame body wherein the first frame body, the second frame body and the cylindrical member are joined integrally and gas-tightly by one of soldering, brazing, and welding between the first frame body and the cylindrical member and between the second frame body and the cylindrical member.

21. The endoscope according to claim 20, wherein plating processing is applied on surfaces of at least one of the first metallic frame body, the second metallic frame body, and the cylindrical member.

22. The endoscope according to claim 21, wherein the plating processing comprises nickel plating on a lower layer, and gold electroplating on an outermost layer.

23. The endoscope for autoclave sterilization according to claim 23, wherein a tip end lens provided at the distal end of the first metallic frame body to be exposed as an outer surface is made of glass having a high temperature vapor resistance, the outer peripheral surface of the tip end lens having been subjected to surface treatment so as to be melted and joined to the first metallic frame body, the tip end lens being air-tightly joined to the first metallic frame body.

24. The endoscope for autoclave sterilization according to claim 23, wherein the outer peripheral surface of the tip end lens has been subjected to a surface treatment so as to form a nickel layer as a lower layer and a gold layer as an upper layer.

25. The endoscope for autoclave sterilization according to claim 23, wherein the outer peripheral surface of the tip end lens has been subjected to a surface treatment so as to form a chrome layer as a lowermost layer, a nickel layer as an intermediate layer and a gold layer as an outermost layer.

26. The endoscope for autoclave sterilization according to claim 23, wherein at least the inner peripheral surface of the metallic frame body is provided with a nickel layer as a lower layer and a gold layer as an upper layer.

27. A method of assembling an endoscope device for autoclave sterilization, comprising steps of:

fitting a second frame body having a solid-state image pickup element therein on an exterior portion of a first frame body having a tip end lens at a distal end thereof and an objective lens system therein such that an outer peripheral surface at the distal end side of the first frame body is exposed from the second frame body;

adjusting the focusing by the objective lens system and the solid-state image pickup element by relatively moving the first frame body and the second frame body in directions along an optical axis;

fitting a cylindrical member on the outer peripheral surface of the first frame body exposed from the second frame body and an outer peripheral surface of the second frame body after having adjusted the focusing; and joining integrally and gas-tightly the first frame body, the second frame body and the cylindrical member by soldering or brazing or welding between the outer peripheral surface of the first frame body and an inner peripheral surface of the cylindrical member and between the outer peripheral surface of the second frame body and the inner peripheral surface of the cylindrical member;

wherein a first frame body includes a joining portion and an optical receiving portion for gas-tightly receiving an optical member, and the second frame body includes a joining portion and an abutting portion positioned rearwardly of the joining portion, an outer diameter of the abutting portion being larger than an outer diameter of the joining portion of the second frame body, the outer diameter of the joining portion of the second frame body being substantially the same as an outer diameter of the optical receiving portion of the first frame body, the joining portion of the first frame body being fitted in an interior of the joining portion of the second frame body, and the cylindrical member is disposed over and gas-tightly joined with the first frame body and the abutting portion of the second frame body, an inner diameter of the cylindrical member being substantially the same as the outer diameters of the optical receiving portion of the first frame body and the joining portion of the second frame body.

28. An endoscope for autoclave sterilization, comprising:

a first frame body having an outer peripheral surface with a outer diameter, the first frame body defining an interior space;

a second frame body having a first outer peripheral surface with a first outer diameter substantially identical to the outer diameter of the outer peripheral surface of the first frame body, the second frame body further having a second outer peripheral surface with a second outer diameter smaller than the first outer diameter of the first outer peripheral surface of the second frame body, the second outer peripheral surface of the second frame body being insertable into the interior space defined by the first frame body;

a third frame body having an inner peripheral surface with a diameter substantially identical to the outer diameter of the outer peripheral surface of the first frame body, the third frame body covering the peripheral surface of the first frame body and the first peripheral surface of the second frame body, the inner peripheral surface of the third frame body being gas-tightly joined to the outer peripheral surface of the first frame body and to the first outer peripheral surface of the second frame body by one of soldering and welding.

29. The endoscope according to claim 28, wherein the third frame body is a cylindrical member.

30. The endoscope according to claim 28, further comprising an image pickup device; and an objective optical system, wherein the first frame body supports the image pickup device, and the second frame body supports the objective optical system, the second frame body being provided at a position to form an image by the objective optical system at the image pickup device.

31. The endoscope according to claim 28, further comprising an image pickup device; and an objective optical system, wherein the second frame body supports the image pickup device, and the first frame body supports the objective optical system, the first frame body being provided at a position to form an image by the objective optical system at the image pickup device.

32. An endoscope for autoclave sterilization; comprising:

a hollow first frame body having an inner peripheral surface with a predetermined diameter;

a second frame body having a first outer peripheral surface slidable along the inner peripheral surface of the first frame body, the second frame body defining an interior space;

a third frame body having a second outer peripheral surface slidable along the inner peripheral surface of the first frame body and a third outer peripheral surface having a diameter smaller than the diameter of the second outer peripheral surface, the third outer peripheral surface being insertable into the interior space defined by the second frame body;

a first joining portion for joining gas-tightly between the inner peripheral surface of the first frame body and the first outer peripheral surface, the first joining portion being joined by one of soldering, bracing and welding; and a second joining portion for joining gas-tightly between the inner peripheral surface of the first frame body and the first outer peripheral surface of the second frame body, the second joining portion being joined by one of soldering, brazing, and welding.

33. The endoscope according to claim 32, wherein the first frame body is a cylindrical member.

34. The endoscope according to claim 32, further comprising an image pickup device; and an objective optical system, wherein the second frame body supports the image pickup device, and the third frame body supports the objective optical system, the third frame body being provided at a position to form an image by the objective optical system at the image pickup device.

35. The endoscope according to claim 32, further comprising an image pickup device; and an objective optical system, wherein the third frame body supports the image pickup device, and the second frame body supports the objective optical system, the second frame body being provided at a position to form an image by the objective optical system at the image pickup device.

36. An endoscope for autoclave sterilization, comprising:

an insertion part having a distal end side;

a hollow first frame body having an inner peripheral surface with a predetermined diameter;

a second frame body provided at the distal end side of the insertion part for supporting an image pickup device therein, the second frame body having a first outer peripheral surface with an outer diameter substantially identical to the predetermined diameter of the inner peripheral surface of the hollow first frame body;

a third frame body to hold an objective optical system therein for forming an image at an imaging plane of the image pickup device, the third frame body having a second outer peripheral surface of an outer diameter substantially identical to the predetermined diameter of the inner peripheral surface of the hollow first frame body;

a first joining portion for joining gas-tightly between the inner peripheral surface of the first frame body and the first outer peripheral surface, the first joining portion being joined by one of soldering, brazing, and welding; and a second joining portion for joining gas-tightly between the inner peripheral surface of the first frame body and the second outer peripheral surface, the second joining portion being joined by one of soldering, brazing, and welding.

37. The endoscope to claim 36, wherein the first frame body is a cylindrical member.

38. An endoscope for autoclave sterilization, comprising:

first frame body having a first outer peripheral surface formed to be of a predetermined diameter, the first frame body holding an objective optical system;

a second frame body for holding an image pickup device for taking an image formed by the objective optical system, a flange portion of a larger diameter than the predetermined diameter being provided on a second outer peripheral surface of the second frame body;

a hollow third frame body having an inner peripheral surface formed to be a predetermined diameter from one end to the other end thereof, the one end of the third frame body abutting against the flange portion, the inner peripheral surface at the side of the other end of the third frame body being fitted to the first outer peripheral surface;

a first joining portion for joining gas-tightly between the inner peripheral surface of the third frame body and the first outer peripheral surface, the first joining portion being joined by soldering or brazing or welding; and a second joining portion for joining gas-tightly between the one end of the third frame body and the flange portion, the second joining portion being joined by soldering or brazing or welding.

39. The endoscope according to claim 38, wherein the third frame body is a cylindrical member.

* * * * *